US00PP29534P2

(12) United States Plant Patent
Guichang et al.

(10) Patent No.: US PP29,534 P2
(45) Date of Patent: Jul. 24, 2018

(54) ***CAMELLIA* PLANT NAMED 'HA351'**

(50) Latin Name: ***Camellia changii* X *Camellia japonica***
Varietal Denomination: HA351

(71) Applicants: Wu Guichang, Guangzhou (CN); Gao Jiyin, Guangzhou (CN); Wang Yaling, Guangzhou (CN)

(72) Inventors: Wu Guichang, Guangzhou (CN); Gao Jiyin, Guangzhou (CN); Wang Yaling, Guangzhou (CN)

(73) Assignee: Palm Eco-Town Development Co. Ltd., Guangzhou (CN)

( * ) Notice: Subject to any disclaimer, the term of this patent is extended or adjusted under 35 U.S.C. 154(b) by 0 days.

(21) Appl. No.: 15/530,359

(22) Filed: Dec. 30, 2016

(51) Int. Cl.
*A01H 5/02* (2018.01)

(52) U.S. Cl.
USPC ..... Plt./245

(58) Field of Classification Search
USPC ..... Plt./245, 244, 243, 226
CPC ..... A01H 5/02; A01H 5/00
See application file for complete search history.

*Primary Examiner* — June Hwu
(74) *Attorney, Agent, or Firm* — C. A. Whealy

(57) ABSTRACT

A new and distinct cultivar of *Camellia* plant named 'HA351', characterized by its sturdy upright plant habit; rapid growth habit; freely branching habit; dense and bushy appearance; leathery dark green-colored leaves; flowering during the summer, autumn and winter; large bright red-colored semi-double flowers; and good garden performance.

2 Drawing Sheets

Botanical designation: *Camellia changii* X *Camellia japonica.*

Cultivar denomination: 'HA351'.

BACKGROUND OF THE INVENTION

The present Invention relates to a new and distinct cultivar of *Camellia* plant, botanically known as *Camellia changii* X *Camellia japonica*, and hereinafter referred to by the name 'HA351'.

The new *Camellia* plant is a product of a planned breeding program conducted by the Inventors in Zhaoqing, China. The objective of the breeding program is to create new fast-growing *Camellia* plants that flower year-round and tolerate full sunlight.

The new *Camellia* plant originated from a cross-pollination conducted by the Inventors in October, 2006 in Zhaoqing, China of an unnamed seedling selection of *Camellia changii*, not patented, as the female, or seed, parent with *Camellia japonica* 'Bob Hope', not patented, as the male, or pollen, parent. The new *Camellia* plant was discovered and selected by the Inventors as a single plant from within the progeny of the stated cross-pollination in a controlled environment in Zhaoqing, China in September, 2011.

Asexual reproduction of the new *Camellia* plant by grafting cuttings onto an unnamed selection of *Camellia gaozhouensis*, not patented, in a controlled greenhouse environment in Zhaoqing, China since has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HA351'. These characteristics in combination distinguish 'HA351' as anew and distinct cultivar of *Camellia:*

1. Sturdy upright plant habit.
2. Rapid growth habit.
3. Freely branching habit, dense and bushy appearance.
4. Leathery dark green-colored leaves.
5. Flowering during the summer, autumn and winter.
6. Large bright red-colored semi-double flowers.
7. Good garden performance, tolerant to full sunlight conditions.

Plants of the new *Camellia* differ from plants of the female parent selection primarily in the following characteristics:

1. Leaves of plants of the new *Camellia* are obovate in shape whereas leaves of plants of the female parent selection are lanceolate in shape.
2. Leaves of plants of the new *Camellia* have sparsely serrate margins whereas leaves of plants of the female parent selection have entire margins.
3. Flowers of plants of the new *Camellia* are larger than flowers of the female parent selection.

Plants of the new *Camellia* differ primarily from plants of the male parent, 'Bob Hope', in the following characteristics:

1. Leaves of plants of the new *Camellia* have sparsely serrate margins whereas leaves of plants of 'Bob Hope' have densely serrate margins.
2. Plants of the new *Camellia* and 'Bob Hope' differ in flower color as plants of 'Bob Hope' have purplish red-colored flowers.

3. Plants of the new *Camellia* flower multiple times during the year whereas plants of plants of 'Bob Hope' flower once a year.

Plants of the new *Camellia* can be compared to the plants of *Camellia* 'Terrell Weaver', not patented. In side-by-side comparisons plants of the new *Camellia* differ from plants of the 'Terrell Weaver' in the following characteristics:

1. Leaves of plants of the new *Camellia* have sparsely serrate margins whereas leaves of plants of 'Terrell Weaver' have densely serrate margins.
2. Plants of the new *Camellia* flower multiple times during the year whereas plants of plants of 'Terrell Weaver' flower once a year.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HA351' grown in a container.

The photograph on the second sheet are close-up view of typical vegetive stems, developing flower buds and developing flowers of 'HA351'.

DETAILED BOTANICAL DESCRIPTION

The aforementioned photographs and following observations and measurements describe plants grown in Zhaoqing, China in an outdoor nursery during the late autumn and under cultural practices typical of commercial *Camellia* production. During the production of the plants, day temperatures averaged 22° C. and night temperatures averaged 18° C. Plants were five years old when the photographs and description were taken. In the following description, color references are made to The Royal Horticultural Society Colour Chart, 2001 Edition, except where general terms of ordinary dictionary significance are used.

Botanical classification: *Camellia changii* X *Camellia japonica* 'HA351'.

Parentage:

*Female, or seed, parent*.—Unnamed seedling selection of *Camellia changii*, not patented.

*Male, or pollen, parent*.—*Camellia japonica* 'Bob Hope', not patented.

Propagation:

*Type*.—By grafting cuttings onto a rootstock, an unnamed selection of *Camellia gaozhouensis*, not patented.

*Time to produce a rooted young plant, summer*.—About two months days at temperatures about 28° C.

*Time to produce a rooted young plant, winter*.—About two months days at temperatures about 8° C.

Plant description:

*Plant form and growth habit*.—Perennial evergreen shrub; sturdy upright plant habit; vigorous growth habit; rapid growth rate.

*Branching habit*.—Freely branching habit; about two to three primary lateral branches each with about three to four secondary branches; dense and bushy appearance.

*Plant height*.—About 173 cm.

*Plant diameter, area of spread*.—About 105 cm.

*Lateral branch description*.—Length: About 158 cm. Diameter: About 7.2 mm. Internode length: About 4 cm to 5 cm. Strength: Strong. Aspect: Upright to about 20° to 30° from vertical. Texture and luster: Smooth, glabrous; matte; woody with development. Color, young stems: Close to 197B; at the internodes, close to 149D. Color, older stems: Close to 199C.

*Leaf description*.—Arrangement: Alternate, single. Length: About 10.5 cm. Width: About 4.2 cm. Shape: Obovate. Apex: Acuminate. Base: Cuneate. Margin: Sparsely serrate. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper and lower surfaces: Close to N199A. Fully expanded leaves, upper surface: Close to N137A; venation, close to 143A; color does not change with the seasons. Fully expanded leaves, lower surface: Close to 147B; venation, close to 147B; color does not change with the seasons.

*Petioles*.—Length: About 1 cm. Diameter: About 2.5 mm. Texture and luster, upper and lower surfaces: Smooth, glabrous; moderately glossy. Color, upper surface: Close to 143A. Color, lower surface: Close to 147B.

Flower description:

*Flower arrangement and appearance*.—Semi-double rotate flowers, flowers terminal and axillary; freely flowering habit with usually about 62 flowers and flower buds developing per plant; flowers face upright to outwardly to nodding.

*Natural flowering season*.—Plants of the new *Camellia* flower during the summer, autumn and winter in Zhaoqing, China.

*Postproduction longevity*.—Plants maintain good flower substance for about eight to ten days on the plant; flowers persistent.

*Fragrance*.—None detected.

*Flower diameter*.—Large, about 12 cm.

*Flower depth*.—About 6 cm.

*Flower buds*.—Length: About 2.5 cm. Diameter: About 2.3 cm. Shape: Ovoid. Texture and luster: Smooth, glabrous; moderately glossy. Color: Close to 138C.

*Petals*.—Quantity and arrangement: About 32 imbricate petals arranged in numerous whorls. Length: About 5.8 cm. Width: About 4 cm. Shape: Broadly obovate. Apex: Obcordate. Base: Cuneate. Margin: Entire; slightly undulate. Texture and luster, upper and lower surfaces: Smooth, glabrous; moderately glossy. Color: When opening, upper and lower surfaces: Close to 46A. Fully opened, upper surface: Close to 46A; venation, close to 46A; color becoming closer to 73A with development. Fully opened, lower surface: Close to 46A; venation, close to 46A; color becoming closer to 47A with development.

*Petaloids*.—Quantity and arrangement: About six at the center of the flower. Length: About 6 cm. Width: About 3.5 cm. Shape: Obovate. Apex: Obcordate. Base: Cuneate. Margin: Entire; moderately undulate. Texture and luster, upper and lower surfaces: Smooth, glabrous; matte. Color: When opening, upper surface: Close to 46A. When opening, lower surface: Close to 46B. Fully opened, upper surface:

Close to 46C; venation, close to 46B; color becoming closer to 46A with development. Fully opened, lower surface: Close to 46A; venation, close to 46B; color becoming closer to 46C with development.

*Sepals*.—Quantity and arrangement: About six imbricate sepals arranged in a shallow cup-shaped calyx. Length: About 1.6 cm. Width: About 1.5 cm. Shape: Broadly elliptical. Apex: Obtuse. Base: Rotund. Margin: Entire. Texture and luster, upper and lower surfaces: Smooth, glabrous; leathery; matte. Color: When opening, upper surface: Close to 145C. When opening, lower surface: Close to 144C. Fully opened, upper and lower surfaces: Close to 145B.

*Peduncles*.—Length: About 6 mm. Diameter: About 4 mm. Aspect: About 25° to 35° from stem axis. Strength: Strong. Texture and luster: Smooth, glabrous; matte. Color: Close to 146A.

*Reproductive organs*.—Androecium: Quantity per flower: About 352. Filament length: About 3.8 cm. Filament color: Close to 38A. Anther shape: Oblong. Anther size: About 2 mm by 1 mm. Anther color: Close to 17A. Pollen amount: Scarce. Pollen color: Close to 17A. Gynoecium: Quantity of pistils per flower: One. Pistil length: About 2.4 cm. Style length: About 2 cm. Style color: Close to 2C. Stigma color: Close to 2C. Ovary color: Close to 2B.

*Fruits and seeds*.—Fruit and seed production have not been observed on plants of the new *Camellia*.

Garden performance: Plants of the new *Camellia* have been observed have good garden performance and to tolerate rain, wind, full sunlight and temperatures ranging from about −10° C. to about 40° C.

Disease & pest resistant: Plants of the new *Camellia* have not been observed to be resistant to pathogens and pests common to *Camellia* plants.

It is claimed:

1. A new and distinct cultivar of *Camellia* plant named 'HA351' as illustrated and described.

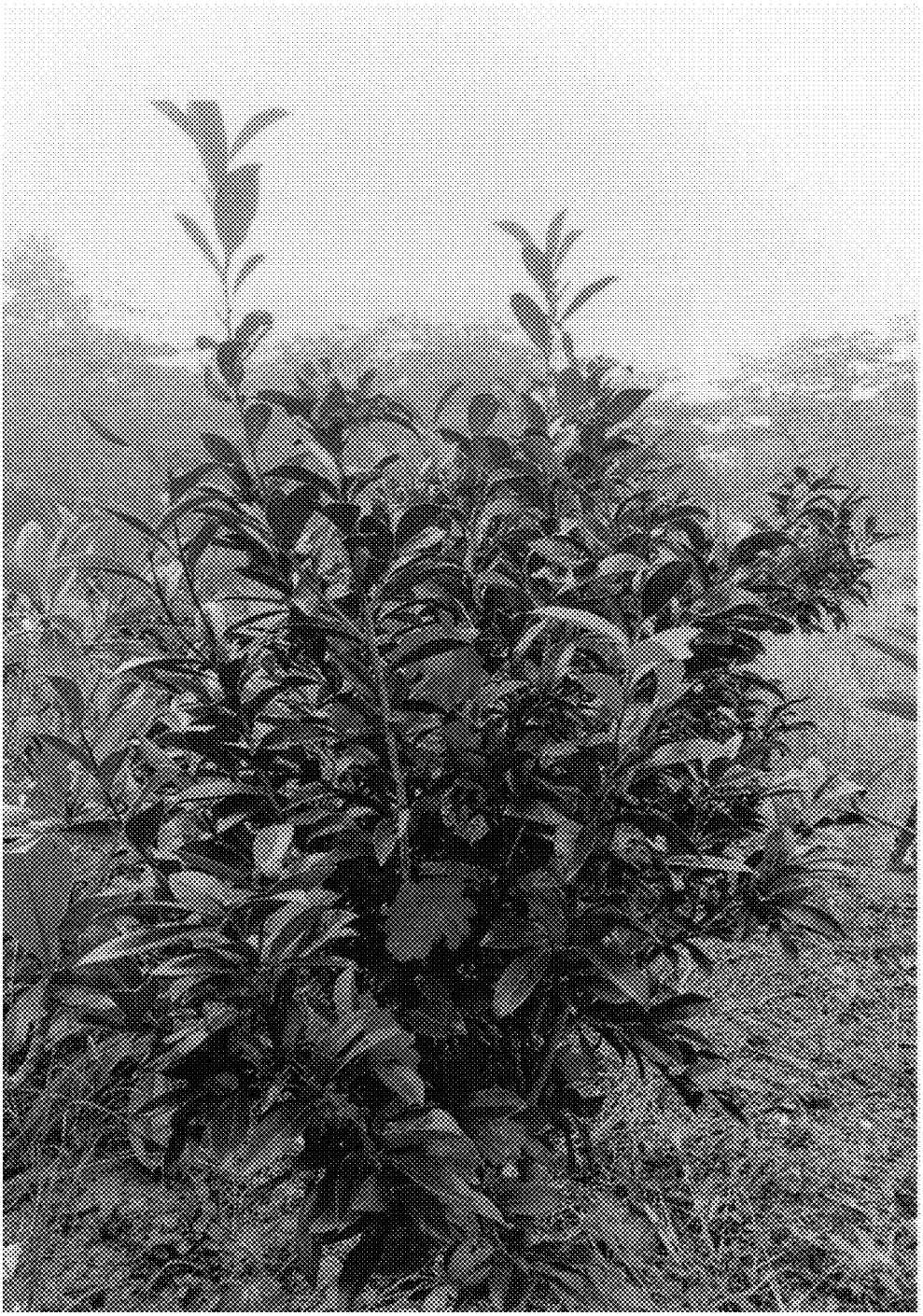

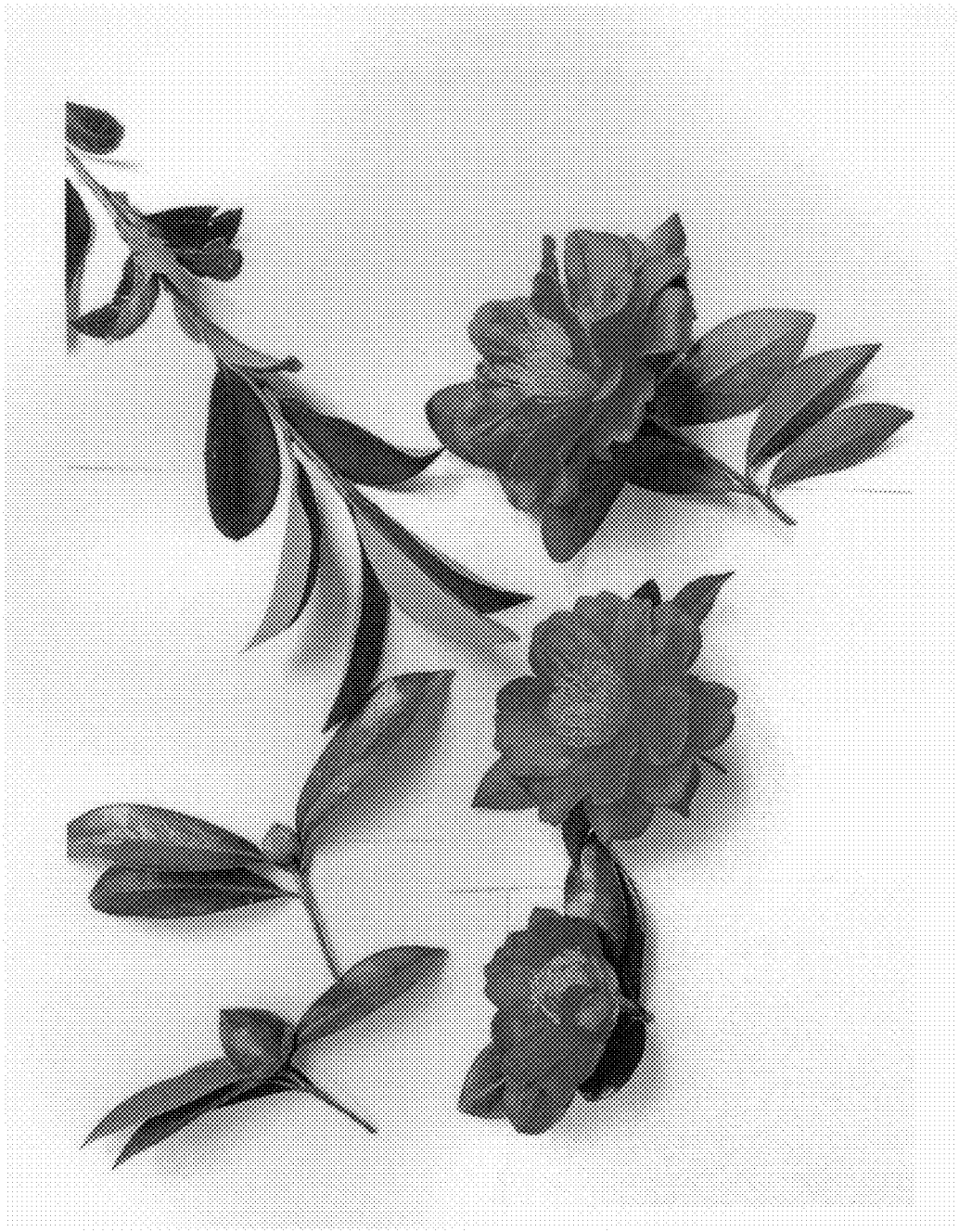

* * * * *